United States Patent [19]

Toda et al.

[11] Patent Number: 5,237,055

[45] Date of Patent: Aug. 17, 1993

[54] CHEMICAL MODIFICATION OF 2"-AMINO GROUP IN ELSAMICIN A

[75] Inventors: Soichiro Toda, Tokyo; Haruhiro Yamashita, Chiba; Takayuki Naito, Kawasaki; Yuji Nishiyama, Tokyo, all of Japan

[73] Assignee: Bristol-Myers Squibb Company, New York, N.Y.

[21] Appl. No.: 836,627

[22] Filed: Feb. 13, 1992

Related U.S. Application Data

[63] Continuation of Ser. No. 707,472, May 30, 1991, abandoned.

[51] Int. Cl.⁵ .................. C07H 5/06; C07H 15/24; C07B 43/00
[52] U.S. Cl. .................. 536/18.5; 536/18.1; 536/16.8; 536/16.1; 536/18.6; 536/55.3; 536/124
[58] Field of Search .......... 536/16.8, 16.1, 18.1, 536/18.5, 18.6, 18.7, 55.3, 124; 514/27, 33, 34, 202

[56] References Cited

U.S. PATENT DOCUMENTS

| | | | |
|---|---|---|---|
| 4,439,433 | 3/1984 | Heymes et al. | 544/22 |
| 4,472,388 | 9/1984 | Umezawa et al. | 514/36 |
| 4,486,418 | 12/1984 | Watanabe et al. | 514/36 |
| 4,499,083 | 2/1985 | Umezawa et al. | 514/36 |
| 4,515,783 | 5/1985 | Linn et al. | 514/27 |
| 4,518,589 | 5/1985 | Konishi et al. | 514/27 |
| 4,562,177 | 12/1985 | Horton et al. | 514/34 |
| 4,927,919 | 5/1990 | Yamada et al. | 536/18.1 |

OTHER PUBLICATIONS

Katrukha et al.; Chemical Abstracts 105:227282d (1986).
Konishi, et al., *J. Antibiotics*, 39: 748–791 (1986).
Sugawara, et al., Elsamicins A and B, new antitumor antibiotics related to chartreusin. 2. Structures of elsamicins A and B. *J. Org. Chem.* 52: 996–1001 (1987).
Leach, et al., Chartreusin, A New Antibiotic Produced by *Streptomyces chartreusis*, a New Species, *J. Am. Chem. Soc.* 75: 4011–4012 (1953).
Beisler, J. A., Chartreusin, A glycosideic Antitumor Antibiotic from Streptomyces, *Progress in Medicinal Chemistry*, Ed., G. P. Ellis and G. B. West 19: pp. 247–268, Elsevier Biomedical Press, Amsterdam, (1982).
Simonitsch et al., Über die Struktur des Chartreusins I, *Helv. Chim. Acta*, 47: 1459–1475, (1964).
Eisenhuth, et al., Über die Struktur des Chartreusins II, *Helv. Chim. Acta*, 47: 1475–1484, (1964).

*Primary Examiner*—Nancy S. Husarik
*Attorney, Agent, or Firm*—Michelle A. Kaye

[57] ABSTRACT

This invention relates to elsamicin A derivatives wherein the 2"-amino group is selectively modified by acylation or alkylation, a process for producing said elsamicin A derivatives, an antitumor composition containing the same as the active ingredient, and a method for therapy using said compositions.

7 Claims, No Drawings

CHEMICAL MODIFICATION OF 2"-AMINO GROUP IN ELSAMICIN A

This is a continuation of application Ser. No. 07/707,472, filed May 30, 1991, now abandoned.

BACKGROUND OF THE INVENTION

1. Field of the Invention

This invention relates to novel elsamicin A derivatives which have better water solubility, improved antitumor activity, and/or reduced toxicity, to their production, to compositions containing the same as the active ingredient, and a method for therapy using said compositions.

2. Description of the Prior Art

Elsamicin A is an antitumor antibiotic produced by cultivating an elsamicin A-producing strain of actinomycete designated strain J907-21 (ATCC 39417), or a mutant thereof. Elsamicin A exhibits antibacterial activity against aerobic gram-positive bacteria and anaerobic bacteria It also exerts activity against various murine tumor cells including leukemia P388, lymphoid leukemia L1210, and melanotic melanoma B16 in vitro and in vivo. Konishi, et al, Elsamicins, new antitumor antibiotics related to chartreusin. I. Production, isolation, characterization and antitumor activity, *J. Antibiotics*, 39: 784–791, (1986); U.S. Pat. No. 4,518,589 to Konishi, et al, issued May 21, 1985.

The structure of elsamicin A (Formula I, below) has been determined and shown to be closely related to chartreusin (Formula II, below). Sugawara, et al, Elsamicins A and B, new antitumor antibiotics related to chartreusin. II. Structures of elsamicins A and B. *J. Org. Chem*, 52: 996–1001, (1987).

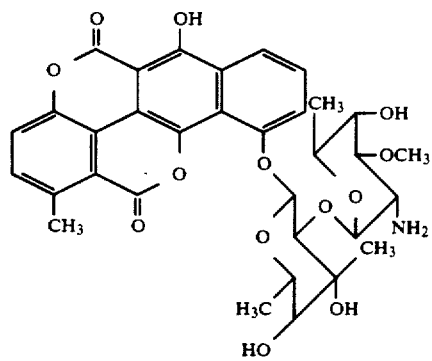

Formula I

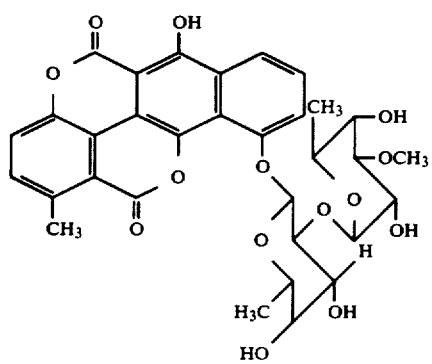

Formula II

Both elsamicin A and chartreusin have the same aglycone, chartarin, but the antibiotics differ in the disaccharide moiety. Leach, et al, Chartreusin, a new antibiotic produced by *Streptomyces chartreusis*, a new species, *J. Am. Chem. Soc.*, 75: 4011–4012, (1953); Beisler, J. A., Chartreusin, A glycosidic antitumor antibiotic for Streptomyces, In progress in Medicinal Chemistry, Ed., G. P. Ellis and G. B. West 19: pp. 247–268, Elsevier Biomedical Press Amsterdam, (1982); Simonitsch, et al: Über die Struktur des Chartreusins I, *Helv. Chim. Acta*, 47: 1459–1475, (1964); Eisenhuth, et al, Über die Struktur des Chartreusins II, *Helv. Chim. Acta*, 47, 1475–1484, (1964). Interconversion of both compounds by chemical process has never been reported.

In the course of chemical modification of elsamicin A, we found that 2"-amino group of elsamicin A was selectively modified by acylation or alkylation to give new elsamicin A derivatives having better water solubility, improved antitumor activity and/or reduced toxicity.

SUMMARY OF THE INVENTION

The present invention provides new derivatives of elsamicin A which exhibit better water solubility, improved antitumor activity and/or reduced toxicity. More particularly the present invention describes the synthesis for 2"-N-alkyl, -acyl and -formimidoyl derivatives of elsamicin A.

This invention further provides an antitumorous composition comprising, as the active ingredient, at least one member selected from the group consisting of the elsamicin A derivative of the present invention.

This invention further provides a method for therapy of cancer using the above antitumorous composition.

Further provided is a process for producing the above-mentioned elsamicin A derivative.

DETAILED DESCRIPTION

U.S. Pat. No. 4,518,589 to Konishi et al, discloses the production and isolation of the antitumor agent designated elsamicin A. (Formula I, above). The above-mentioned elsamicin A compound is the principal component of the fermentation of the elsamicin A-producing strain of actinomycete, designated strain J907-21 (ATCC 39417).

It has now been found according to the present invention that acylation or alkylation of the 2"-amino group of elsamicin A gave new derivatives having improved antitumor activity, better water solubility and/or lower toxicity.

The elsamicin A derivatives of the present invention have the general Formula III and IV below

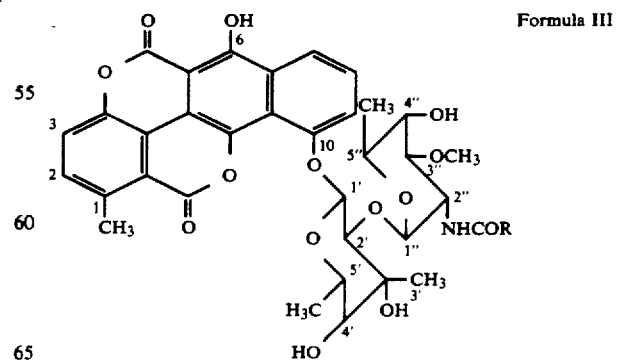

Formula III wherein R is $C_1$–$C_3$ alkyl, non-substituted or substituted with carboxyl, amino or phthalimido;

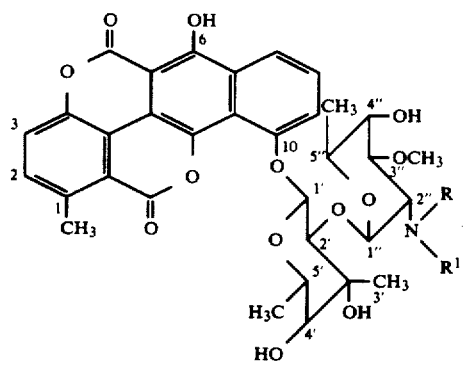

Formula IV wherein R and R[1] independently represent hydrogen, $C_1$–$C_3$ alkyl, aralkyl, formimidoyl, acetimidoyl or amidinyl, with the proviso that both R and R[1] can not be hydrogen at the same time and that R and R[1] when taken together with the nitrogen atom to which they are attached, may be morpholino, piperidino or pyrrolidino.

The term "$C_1$–$C_3$ alkyl" as used herein and in the claims (unless the context indicates otherwise) means branched or straight chain hydrocarbon group having 1 to 3 carbon atoms such as methyl, ethyl, propyl and isopropyl.

The compounds of this invention may be produced, for example, by the synthetic process diagrammed in Tables 2 and 3. As shown in Table 2, elsamicin A was N-acylated with acetic acid and succinic acid by the acid anhydride method to give compounds 3a and 3b, respectively, The N-glycyl derivative 3d was prepared by acylation with an active ester of phthalyl glycine and subsequent deprotection with hydrazine in a good yield.

As shown in Table 3, reductive N-alkylation of elsamicin A with aldehydes or a ketone gave N-alkyl derivatives. The reaction of elsamicin A with acetone in the presence of sodium cyanoborohydride ($NaBH_3CN$) gave N-isopropylelsamicin A (4a). The reaction of elsamicin A with an excess of formaldehyde and $NaBH_3CN$ gave N,N-dimethylelsamicin A (4e) in a 54% yield. As the N-methylation with a limited amount of formaldehyde and $NaBH_3CN$ still gave a mixture of amino, monomethylamino and dimethylamino derivatives, N-monomethylation of elsamicin A was attempted by a similar procedure to that employed in the preparation of N-monomethylamikacin derivatives. Thus, elsamicin A was treated with 2,4-dimethoxybenzaldehyde and $NaBH_3CN$ to give N-(2,4-dimethoxy)-benzyl derivative (4b), which was subjected to reductive N-methylation with formaldehyde and $NaBH_3CN$ to afford the N-(2,4-dimethoxy)benzyl-N-methyl derivative (4c). De-benzylation of 4c by catalytic hydrogenation gave N-monomethylelsamicin A (4d). Preparation of morpholino derivative (4f) of elsamicin A was also carried out by treatment of elsamicin A with 2,2′-oxydiacetaldehyde and $NaBH_3CN$.

The formimidoyl derivative was prepared by the conventional method, i.e., treatment of elsamicin A with ethyl formimidate hydrochloride gave compound 5 in 38% yield.

Table 1 indicates the compounds of the present application and their respective number.

TABLE 1

| Compound of the present invention and their respective number | |
|---|---|
| Compound No. | Name |
| 1 | Elsamicin A |
| 2 | Chartreusin |
| 3a | 2″-N-Acetylelsamicin A |
| 3b | 2″-N-(3-Carboxypropionyl)elsamicin A |
| 3c | 2″-N-(Phthalimidoacetyl)elsamicin A |
| 3d | 2″-N-Glycylelsamicin A |
| 4a | 2″-N-Isopropylelsamicin A |
| 4b | 2″-N-(2,4-Dimethoxybenzyl)elsamicin A |
| 4c | 2″-N-(2,4-Dimethoxybenzyl)-2″-N-methyl-elsamicin A |
| 4d | 2″-N-Methylelsamicin A |
| 4e | 2″-N,N-Dimethylelsamicin A |
| 4f | 2″-Deamino-2″-morpholinoelsamcin A |
| 5 | 2″-N-Formimidoylelsamicin A hydrochloride |

TABLE 2

N-Acylation of elsamicin A

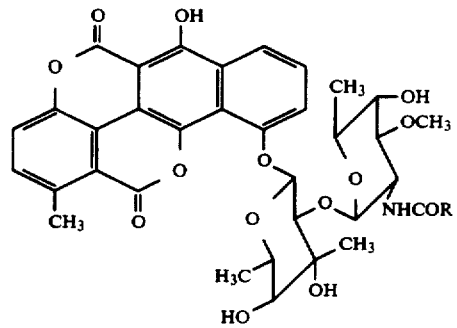

| | Product | |
|---|---|---|
| Reaction | No. | R |
| 1 + Ac₂O | 3a | $CH_3$ |
| 1 + (succinic anhydride) | 3b | $CH_2CH_2COOH$ |

TABLE 2-continued

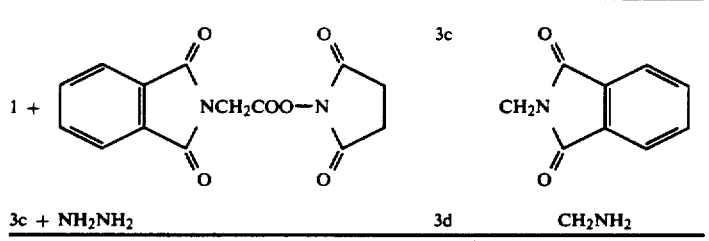

| Reaction | No. |
|---|---|
| 3c + NH₂NH₂ | 3d |

TABLE 3

N-alkylation and formimidation of elsamicin A

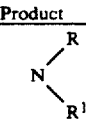

| Reaction | No. | Product $-N{<}^R_{R^1}$ |
|---|---|---|
| 1 + CH₃COCH₃ + NaBH₃CN | 4a | —NHCH(CH₃)₂ |
| 2 + CH₃O-C₆H₃(OCH₃)-CHO + NaBH₃CN | 4b | —NHCH₂-C₆H₃(OCH₃)(OCH₃) |
| 4b + HCHO + NaBH₃CN | 4c | —N(CH₃)CH₂-C₆H₃(OCH₃)(OCH₃) |
| 4c + H₂/Pd—C | 4d | —NHCH₃ |
| 1 + HCHO + NaBH₃CN | 4e | —N(CH₃)₂ |
| 1 + O(CH₂CHO)₂ + NaBH₃CN | 4f | —N(morpholino) |
| 1 + NH=CHOEt.HCl | 5 | —NHCH=NH |

Antitumor activity of 2″-N-alkyl, -acyl and -formimidoylelsamicin A derivatives Eight 2″-N-alkyl, -acyl or -formimidoylelsamicin A derivatives were synthesized and comparatively tested with the parent compound for in vitro cytotoxicity against B16 melanoma cells and in vivo antitumor activity against P388 leukemia and B16 melanoma.

For in vitro cytotoxicity experiment, murine melanoma B16-F10 cells were grown and maintained in Eagle's minimum essential medium (Nissui), which contains kanamycin (60 μg/ml), supplemented with heat-inactivated fetal calf serum (10%) and nonessential amino acids (0.6%) at 37° C. under a humidified atmosphere in a 5% CO₂ incubator. Exponentially growing B16-F10 cells were harvested, counted and suspended in the culture medium at the concentration of 2.0×10⁴ cells/ml. The cell suspension (180 μl) was planted into wells of a 96-well microtiter plate and incubated for 24 hours. Test compounds (20 μl) were added to the wells and the plates were further incubated for 72 hours. The cytotoxic activity was colorimetrically determined at 540 nm after staining viable cells with neutral red solution. All of the derivatives tested gave moderate and less in vitro cytotoxicity against B16-F10 cells than elsamicin A (Table 4).

Among the derivatives tested, in vivo antitumor activity of six derivatives showing relatively potent cytotoxicity was tested in the lymphocytic leukemia P388 and B16 melanoma systems. Female CDF$_1$ (for P388) and male BDF$_1$ (for B16) mice were inoculated by ip injection at $10^6$ P388 cells and 0.5 ml of a 10% B16 brei per mouse, respectively (day 0). Test compounds were intraperitoneally administered to the mice once daily on days 1 to 3 (Q1Dx3) in the P388 system or once a day on days 1, 5 and 9 (Q4Dx3) in the B16 system and animals were observed for 50 days. The percent increase of median survival time (MST) of treated animals over that of untreated control animals was determined and reported as T/C %. Compounds showing T/C % values of 125 or greater are considered to have significant antitumor activity. As shown in Table 4, 2''-N-isopropylelsamicin A, (4a), 2''-N-methylelsamicin A, (4d), 2''-N,N-dimethylelsamicin A, (4e) and 2''-N-formimidoylelsamicin A HCl, (5) were 10-30 times less active than the parent compound in terms of minimum effective doses (MED) and showed quite limited prolongation of life-span in the P388-bearing mice. The others had no activity at the doses tested. Derivatives 4d, 4e, and 5 when tested in the B16 system, also gave 10-30 times less antitumor activity than elsamicin A in terms of MED (Table 5).

The present invention includes within its scope a process for producing the elsamicin A derivatives of the present invention.

Another aspect of the invention, there are provided pharmaceutical compositions which comprise an effective tumor-inhibiting amount of the compound of Formula III or IV, in combination with an inert pharmaceutically acceptable carrier or diluent.

According to another aspect of the invention provides a method for therapeutically treating an animal, preferably mammalian, host affected by a tumor which comprises administering to such host an effective tumor-inhibiting dose of the antibiotic of the compound of Formula III or IV.

Examples of suitable compositions include solid compositions for oral administration such as tablets, capsules, pills, powders and granules, liquid compositions for oral administration such as solutions, suspensions, syrups and elixirs and preparations for parenteral administration such as sterile solutions, suspensions or emulsions. They may also be manufactured in the form of sterile solid compositions which can be dissolved in sterile water, physiological saline or some other sterile injectable medium immediately before use.

It will be appreciated that the actual preferred dosages of the elsamicin A derivative of the present invention will vary according to the particular compound being used, the particular composition formulated, the mode of application and the particular situs, host and disease being treated. Many factors that modify the action of the drug will be taken into account by those skilled in the art, e.g. age, body weight, sex, diet, time of administration, rate of excretion, condition of the host, drug combinations, reaction sensitivities and severity of the disease. Administration can be carried out continuously or periodically within the maximum tolerated dose. Optimal application rates for a given set of conditions can be readily ascertained by those skilled in the art using conventional dosage determination tests.

The present invention is illustrated by the following examples which are not intended to be construed as limiting the scope of the invention.

TABLE 4

In vitro cytotoxicity against B16-F10 melanoma and in vivo antitumor activity against P388 leukemia in mice

| Compound | R or $-N{\scriptstyle\begin{array}{c}R\\R^1\end{array}}$ | Cytotoxicity IC$_{50}$ (μg/ml) | T/C % of MST[1] | | | | |
|---|---|---|---|---|---|---|---|
| | | | 20[2] | 10 | 3 | 1 | 0.3 | 0.1 |
| 3a | CH$_3$ | 55 | | Not | done | | | |
| 3b | CH$_2$CH$_2$COOH | 56 | | Not | done | | | |
| 3d | CH$_2$NH$_2$ | 4.1 | | 110 | 110 | 95 | | |
| 4a | —NHCH(CH$_3$)$_2$ | 1.5 | | 140 | 120 | 110 | | |
| 4d | —NHCH$_3$ | 1.7 | | 145 | 130 | 120 | 100 | 100 |
| 4e | —N(CH$_3$)$_2$ | 0.36 | | 140 | 130 | 110 | | |
| 4f | 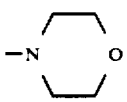 | 11 | | 100 | 105 | 100 | | |
| 5 | —NHCH=NH | 0.47 | | 140 | 130 | 120 | 100 | 100 |
| Elsamicin A (1) | | 0.07 | Tox | 205 | 170 | 150 | 137 | 120 |

[1] Median survival time in days
[2] Dose in mg/kg/day, Q1Dx3, ip

TABLE 5

In vivo antitumor activity against B16 melanoma in mice

| | T/C % of MST[1] | | | | |
|---|---|---|---|---|---|
| Compound | 10[2] | 3 | 1 | 0.3 | 0.1 |
| 4d | 135 | 115 | 100 | 106 | |
| 4e | 132 | 109 | 103 | | |
| 5 | 150 | 126 | 103 | 100 | |
| 1 | ≥282 (4/8)[3] | 208 | 168 | 128 | 115 |

[1] Median survival time in days
[2] Dose in mg/kg/day, Q4Dx3 ip
[3] No. of survivors/tested on day 50

EXAMPLE 1

Synthesis of 2"-N-Acetylelsamicin A (3a)

A mixture of elsamicin A (65.4 mg) and acetic anhydride (0.1 ml) in dry methanol (2 ml) was stirred at room temperature for 1 hour. Water (1 ml) was added and the mixture was evaporated in vacuo to give a yellow oil, which was purified by column chromatography on silica gel to give 70.5mg (100%) of the desired product.

MP 195°-196° C. IR $\nu_{max}$ (KBr) cm$^{-1}$ 3420, 1725, 1690, 1615, 1510, 1380, 1255, 1240, 1170, 1120. UV $\lambda_{max}$ (MeOH) nm ($\epsilon$) 236 (35,200), 265 (34,500), 333 (6050), 379 (8000), 400 (13,400), 423 (14,800). $^1$H NMR (CDCl$_3$) $\delta$ 0.88 (3H, s), 1.38 (9H, m), 2.68 (3H, s), 3.32 (3H, s), 5.36 (1H, d, J=7 Hz), 5.70 (1H, d, J=4 Hz).

Anal. Calcd. for $C_{35}H_{37}NO_{14} \cdot H_2O$:
C 58.90, H 5.51, N 1.96.
Found: C 58.59, H 5.36, N 2.10.

EXAMPLE 2

Synthesis of 2"-N-(3-Carboxypropionyl)elsamicin A (3b)

A mixture of elsamicin A (65.4 mg) and succinic anhydride (20 mg) in dry dioxane (6.5 ml) was stirred at room temperature for 3 hours. Methanol (3 ml) was added at 5° C. and the mixture was evaporated to dryness. The residue was purified by preparative TLC developing with CH$_2$Cl$_2$: MeOH: AcOH=80:20:2 to give 75 mg of yellow powder, which was dissolved in diluted aqueous NaHCO$_3$ solution. The solution was adjusted at pH3 and chromatographed on a column of Diaion HP-20. The column was successively eluted with H$_2$O and 50% aqueous CH$_3$CN. The fractions containing the desired product were combined, evaporated and lyophilized to give 44 mg (55%) of compound 3b as a yellow powder.

MP 198°-200° C. (dec.) IR $\nu_{max}$ (KBr) cm$^{-1}$ 3400, 1715, 1640, 1610, 1505. UV $\lambda_{max}$ (MeOH) nm ($\epsilon$) 236 (39,700), 265 (39,900), 334 (6010), 380 (8350), 400 (13,800), 423 (16,000). $^1$H NMR (CD$_3$OD) $\delta$ 2.83 (3H, s), 3.30 (3H, s), 5.52 (1H, d, J=8 Hz), 5.83 (1H, d, J=4 Hz), 8.15 (1H, d, J=8 Hz).

Anal. Calcd. for $C_{37}H_{33}NO_{16}Na \cdot 3/2\ H_2O$:
C 55.36, H 5.15, N 1.74.
Found: C 55.40, H 4.87, N 1.92.

EXAMPLE 3

Synthesis of 2"-N-(Phthalimidoacetyl)elsamicin A (3c)

To a solution of elsamicin A (65.5 mg) in dioxane (4 ml) were added N-hydroxysuccinimide ester of phthaloylglycine (60.4 mg) and NEt$_3$ (20 mg). The mixture was stirred at room temperature for 2 days and evaporated in vacuo. The residue was triturated with water to give a yellow solid, which was purified by column chromatography on silica gel to give 76 mg (90%) of compound 3c.

MP 187°-189° C. IR $\nu_{max}$ (KBr) cm$^{-1}$ 1770, 1715, 1250, 1140, 1110, 1065, 775. UV $\lambda_{max}$ (MeOH) nm ($\epsilon$) 220 (56,700), 235 (47,600), 266 (37,000), 333 (6050), 379 (8480), 399 (14,200), 422 (15,700). $^1$H NMR (CD$_3$OD) $\delta$ 1.32 (3H, d, J=6 Hz), 1.43 (3H, d, J=6 Hz), 1.45 (3H, s), 2.78 (3H, s), 3.30 (3H, s), 5.58 (1H, d, J=8 Hz), 5.90 (1H, d, J=4 Hz), 7.08 (4H, s).

Anal. Calcd. for $C_{43}H_{40}N_2O_{16} \cdot 2H_2O$:
C 58.90, H 5.06, N 3.19.
Found: C 58.71, H 4.71, N 3.03.

EXAMPLE 4

Synthesis of 2"-N-Glycylelsamicin A (3d)

To a solution of the phthalimido derivative 3c (62 mg) in EtOH (0.5 ml) was added 80% aqueous NH$_2$NH$_2$ (10 $\mu$l) and the mixture was kept at room temperature for 6 hours and concentrated in vacuo. The residue was purified by preparative TLC developing with 2% MeOH in CHCl$_3$ to give 52 mg of a solid. The solid was further purified by column chromatography on HP-20 to give 45 mg (86%) of compound 3d.

MP 203°-210° C. (dec.). IR $\nu_{max}$ (KBr) cm$^{-1}$ 1685, 1375, 1250, 1150, 1110, 1070, 1045, 775. UV $\lambda_{max}$ (MeOH) nm ($\epsilon$) 236 (37,000), 266 (32,900), 332 (5540), 379 (7530), 400 (12,400), 422 (13,900). $^1$H NMR (CD$_3$OD) $\delta$ 1.32 (3H, d, J=6 Hz), 1.40 (3H, s), 1.41 (3H, d, J=6 Hz), 1.82 (2H, s), 2.80 (3H, s), 3.30 (3H, s), 5.46 (1H, d, J=8 Hz), 5.81 (1H, d, J=4 Hz). EI-MS (in beam): m/z: 710 (M+), 494, 376, 334, 217.

EXAMPLE 5

Synthesis of 2"-N-Isopropylelsamicin A (4a)

A mixture of elsamicin A (65.4 mg), acetone (0.1 ml) and NaBH$_3$CN (30 mg) in dioxane (5 ml) was stirred at room temperature for 17 hours. The reaction mixture was evaporated in vacuo to give a yellow mass, which was dissolved in diluted aqueous HCl and subjected to a column of Diaion HP-20 eluting with 50% methanol. The fractions containing the desired product were combined and evaporated to give a yellow powder, which was further purified by preparative TLC to give 19 mg (27%) of the title compound.

MP 175°-180° C. (dec.). IR $\nu_{max}$ (KBr) cm$^{-1}$ 3430, 1690, 1610, 1505, 1370, 1250, 1145, 1110, 1040, 780. UV $\lambda_{max}$ (MeOH) nm ($\epsilon$) 237 (44,000), 265 (39,100), 333 (6840), 378 (9370), 398 (14,900), 421 (17,100). $^1$H NMR (CDCl$_3$) $\delta$ 0.28 (3H, d, J=7 Hz), 0.52 (3H, d, J=7 Hz), 1.33 (9H, m), 2.64 (3H, s) 3.41 (3H, s), 5.48 (1H, d, J=7 Hz), 5.58 (1H, d, J=4 Hz). EI-MS (in beam): m/z: 334, 202.

EXAMPLE 6

Synthesis of 2"-N-(2,4-Dimethoxybenzyl)elsamicin A (4b)

To a solution of elsamicin A (65 mg) and 2,4-dimethoxybenzaldehyde (85 mg) in 70% aqueous CH$_3$CN (5 ml) was added NaBH$_3$CN (30 mg) and the mixture was stirred at room temperature overnight, diluted with 1N aqueous HCl and extracted with CHCl$_3$. The organic extract was washed with 1N aqueous NH$_4$OH, dried over Na$_2$SO$_4$ and evaporated in vacuo. The residue was triturated with aqueous t-BuOH to give 44 mg (55%) of the title compound as crystals Another crop (35 mg, 44%) was obtained from the mother liquor by lyophilization.

MP 159°-161° C. IR $\nu_{max}$ (KBr) cm−1 3400, 1659, 1615, 1510, 1370, 1250, 1210, 1105, 1075, 1045, 780. UV $\lambda_{max}$ (MeOH) nm ($\epsilon$) 235 (35,300), 267 (28,900), 336 (5080), 401 (10,900), 424 (12,300). $^1$H NMR (CDCl$_3$) $\delta$ 1.33 (3H, d, J=6 Hz), 1.40 (3H, d, J=6 Hz), 1.44 (3H, s), 2.78 (3H, s), 3.06 (3H, s), 3.39 (3H, s), 3.53 (3H, s), 5.28 (1H, dd, J=8 & 2 Hz), 5.52 (1H, d, J=8 Hz), 5.64 (1H, d, J=2 Hz), 5.85 (1H, d, J=4 Hz), 6.32 (1H, d, J=8 Hz).

Anal. Calcd. for $C_{42}H_{45}NO_{15} \cdot 3/2H_2O$:
C 60.71, H 5.82, N 1.69.

Found: C 60.89, H 6.39, N 1.72.

EXAMPLE 7

Synthesis of 2''-N-(2,4-Dimethoxybenzyl)-2''-N-methylelsamicin A (4c)

To a mixture of the N-benzyl derivative (4b) (119 mg) and 37% aqueous HCHO (47 mg) in 70% aqueous $CH_3CN$ (2.4 ml) was added $NaBH_3CN$ (47 mg), and the mixture was stirred at room temperature for 22 hours. The reaction mixture was diluted with 1N HCl and extracted with $CHCl_3$. The extract was washed with 1N $NH_4OH$ and evaporated under reduced pressure. The residue was purified by column chromatography on silica gel to give 105 mg (87%) of the monomethyl derivative 4c.

MP 141°-143° C. IR $\nu_{max}$ (KBr) cm$^{-1}$ 3400, 1720 (sh), 1690, 1505, 1375, 1250, 1070, 1050, 780. UV $\lambda_{max}$ (MeOH) nm ($\epsilon$) 235 (42,800), 267 (33,500), 335 (5580), 381 (7700), 400 (12,100), 422 (14,100). $^1$H NMR (CDCl$_3$) $\delta$ 1.25 (3H, d, J=6 Hz), 1.39 (3H, d, J=6 Hz), 1.40 (3H, s), 2.28 (3H, s), 2.58 (3H, s), 3.40 (3H, s), 3.47 (3H, s), 3.60 (3H, s), 5.40 (1H, d, J=8 Hz), 5.60 (1H, d, J=4 Hz), 5.72 (1H, dd, J=8 & 2 Hz) 6.12 (1H, d, J=2 Hz), 6.73 (1H, d, J=8 Hz).

Anal. Calcd. for $C_{43}H_{47}NO_{15} \cdot H_2O$:
C 61.79, H 5.91, N 1.68.
Found: C 61.75, H 5.94, N 2.40.

EXAMPLE 8

Synthesis of 2''-N-Methylelsamicin A (4d)

A solution of 4c (100 mg) in a mixture of 70% aqueous THF (3 ml) and 1N HCl (0.8 ml) was hydrogenated in the presence of 10% Pd-C (100 mg) at room temperature for 7 hours under atmospheric pressure. The catalyst was removed by filtration and the filtrate was evaporated in vacuo. The residue was purified by column chromatography on silica gel to give 52 mg (61%) of the title compound.

MP 192°-194° C. (dec.). IR $\nu_{max}$ (KBr) cm$^{-1}$ 3400, 1690, 1375, 1250, 1070, 1045, 780. UV $\lambda_{max}$ (MeOH) nm ($\epsilon$) 236 (34,100), 266 (29,800), 332 (5430), 337 (6820), 398 (10,600), 420 (11,700). $^1$H NMR (CDCl$_3$+CD$_3$OD) $\delta$ 1.23 (3H, d, J=6 Hz), 1.28 (3H, d, J=6 Hz), 1.40 (3H, s), 2.36 (3H, s), 2.82 (3H, s), 3.43 (3H, s), 5.61 (1H, d, J=8 Hz), 5.92 (1H, d, J=4 Hz). SI-MS: m/z 668 (M+H)$^+$, 334, 174, 100.

EXAMPLE 9

Synthesis of 2''-N,N-Dimethylelsamicin A (4e)

To a mixture of elsamicin A (65.5 mg) and 37% aqueous HCHO (85 $\mu$l) in dioxane (4 ml) was added NaBH$_3$CN (30 mg) and the mixture was stirred at room temperature for 3 hours. The reaction mixture was evaporated in vacuo to give a yellow solid, which was chromatographed on a silica gel column. The fractions containing the desired product were combined and concentrated to dryness. The residue was purified by preparative ILC to give 36.7 mg (54%) of the dimethyl derivative 4e.

MP 180°-185° C. IR $\nu_{max}$ (KBr) cm$^{-1}$ 1720, 1700, 1690, 1505, 1375, 1235, 1145, 775 UV $\lambda_{max}$ (MeOH) nm ($\epsilon$) 236 (37,200), 266 (33,600), 333 (5650), 379 (7700), 399 (12,500), 422 (13,800). $^1$H NMR (CD$_3$OD) $\delta$ 1.30 (3H, d, J=6 Hz), 1.31 (3H, d, J=6 Hz), 1.39 (3H, s), 2.05 (6H, s), 2.72 (3H, s), 3.36 (3H, s), 5.50 (1H, d, J=8 Hz), 5.85 (1H, d, J=4 Hz).

Anal. Calcd. for $C_{35}H_{39}NO_{13} \cdot 2H_2O$:
C 58.57, H 6.04, N 1.95.
Found: C 58.32, H 5.79, N 2.07.

EXAMPLE 10

Synthesis of 2''-Deamino-2''-morpholinoelsamicin A (4F)

To a mixture of elsamicin A (98.5 mg) and 2,2'-oxydiacetaldehyde, prepared by ozonolysis of 2,5-dihydrofuran in CH$_3$CN (4.5 ml) was added NaBH$_3$CN (47 mg) and the mixture was stirred at room temperature for 1.5 hours. The organic solvent was evaporated in vacuo and the residual aqueous solution was chromatographed on a column of HP-20. The fractions containing the desired product were combined and evaporated in vacuo to give a yellow mass, which was purified by preparative TLC to obtain 35.5 mg (33%) of the desired product.

MP 182°-186° C. (dec.). IR $\nu_{max}$ (KBr) cm$^{-1}$ 1720, 1690, 1375, 1255, 1235, 1150, 1120, 1070, 780. UV $\lambda_{max}$ (MeOH) nm ($\epsilon$) 236 (39,400), 265 (38,800), 334 (6440), 379 (8790), 400 (15,000), 423 (16,800). $^1$H NMR (CD$_3$OD) $\delta$ 1.28 (3H, d, J=6 Hz), 1.38 (3H, s), 1.42 (3H, d, J=6 Hz), 2.80 (3H, s), 3.3 (3H, s), 5.38 (1H, d, J=8 Hz), 5.78 (1H, d, J=4 Hz). EI-MS (in beam) m/z 723 (M+), 492, 389, 334, 230.

Anal. Calcd. for $C_{37}H_{41}NO_{14} \cdot 2H_2O$:
C 58.49, H 5.97, N 1.84.
Found: C 58.60, H 5.48, N 1.94.

EXAMPLE 11

Synthesis of 2''-N-Formimidoylelsamicin A hydrochloride (5)

To a suspension of elsamicin A (131 mg) in a mixture of CHCl$_3$ and MeOH (9: 1, 4 ml) was added ethyl formimidate hydrochloride (66 mg) at 0° C., and the mixture was stirred at room temperature for 39 hours. MeOH (8 ml) and acetic acid (2 ml) were added to the reaction mixture and the clear solution was stirred at room temperature for 0.5 hour and evaporated in vacuo. The residue was purified by preparative TLC to give 52 mg (38%) of compound 5.

MP 228°-230° C. (dec.). IR $\nu_{max}$ (KBr) cm$^{-1}$ 3380, 1710, 1630, 1610, 1590, 1505, UV $\lambda_{max}$ (MeOH) nm ($\epsilon$) 237 (40,900), 266 (37,400), 333 (6640), 379 (8930), 399 (14,500), 422 (16,400). $^1$H NMR (CDCl$_3$+CD$_3$OD) $\delta$ 1.0-1.6 (9H, m), 2.60 (3H, s), 3.35 (3H, s), 5.65 (1H, d, J=8 Hz), 5.85 (1H, brs).

Anal. Calcd. for $C_{34}H_{36}N_2O_{13} \cdot 3HCl$:
C 51.69, H 4.98, N 3.55.
Found: C 51.57, H 4.74, N 3.52.

What is claimed is:

1. A process for producing the compounds having the formula

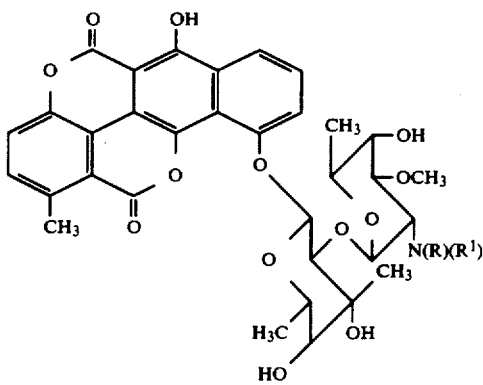

wherein N(R)(R¹) is NHCH(CH₃)₂, N(CH₃)₂, NHCH=NH, NHCH₂(C₆H₆)(OCH₃)₂, or N(CH₃)CH₂(C₆H₆)(OCH₃)₂, which comprises reductive N-alkylation of elsamicin A with aldehydes or ketones, in sodium cyanoborohydride, stirring at room temperature, evaporating, and purification by chromatography.

2. A process for producing 2''-N-formimidoylelsamicin A hydrochloride which comprises treating elsamicin A with ethyl formimidate hydrochloride, at 0° C., stirring at room temperature, evaporating, followed by purification.

3. The process for producing 2''-N-methylelsamicin A which comprises debenzylation of 2''-N-(2,4-dimethoxybenzyl)-2''-N-methylelsamicin A, by catalytic hydrogenation, removing the catalyst by filtration and evaporation, followed by purification by column chromatography.

4. The process for producing 2''-deamino-2''-morpholinoelsamicin A which comprises adding sodium cyanoborohydride to a mixture of elsamicin A with 2,4'-oxydiacetaldehyde, stirring at room temperature, evaporating, and purification by column chromatography.

5. The process for producing 2''-N-(3-carboxypropionyl)elsamicin A which comprises N-acylation of elsamicin A with succinic anhydride in dry dioxane, stirring at room temperature, adding methanol at 5° C., evaporating, and purification by preparative thin-layer chromatography.

6. The process for producing 2''-N-(phthalimidoacetyl)elsamicin A which comprises N-acylation of elsamicin A with an active ester of phthaloylglycine, then stirring at room temperature, evaporating, and purification by column chromatography.

7. The process for producing 2''-glycylelsamicin A which comprises adding hydrazine to a solution of 2''-N-(phthalimidoacetyl)elsamicin A in ethanol, maintaining at room temperature, concentrating, and purification by preparative thin-layer chromatography.

* * * * *

UNITED STATES PATENT AND TRADEMARK OFFICE
CERTIFICATE OF CORRECTION

PATENT NO. : 5,237,055
DATED : August 17, 1993
INVENTOR(S) : Toda, et al.

It is certified that error appears in the above-indentified patent and that said Letters Patent is hereby corrected as shown below:

Column 14, Claim 4, line 10, after "2," please delete "4" and insert --2--.

Signed and Sealed this

Eighth Day of March, 1994

*Attest:*

BRUCE LEHMAN

*Attesting Officer*    *Commissioner of Patents and Trademarks*